United States Patent [19]
Lillwitz et al.

[11] Patent Number: 5,334,796
[45] Date of Patent: * Aug. 2, 1994

[54] ALKYLATION OF ALKYLAROMATICS PROMOTED BY AMINE COMPOUND

[75] Inventors: Lawrence D. Lillwitz, Glen Ellyn; Anne M. Karachewski, St. Charles, both of Ill.

[73] Assignee: Amoco Corporation, Chicago, Ill.

[*] Notice: The portion of the term of this patent subsequent to Mar. 30, 2010 has been disclaimed.

[21] Appl. No.: 20,334

[22] Filed: Feb. 19, 1993

Related U.S. Application Data

[63] Continuation of Ser. No. 799,543, Nov. 27, 1991, Pat. No. 5,198,594.

[51] Int. Cl.$^5$ .............................................. C07C 2/66
[52] U.S. Cl. ..................................... 585/467; 585/452
[58] Field of Search ....................... 585/467, 452, 446

[56] References Cited

U.S. PATENT DOCUMENTS

| | | | |
|---|---|---|---|
| 3,705,200 | 12/1972 | Bunting et al. | 585/452 |
| 3,766,288 | 10/1973 | Shima et al. | 585/446 |
| 4,982,034 | 1/1991 | Moore et al. | 585/446 |
| 5,198,594 | 3/1993 | Lillwitz et al. | 585/452 |
| 5,210,353 | 5/1993 | Udovich et al. | 585/459 |

Primary Examiner—Anthony McFarlane
Attorney, Agent, or Firm—Thomas E. Nemo; Wallace L. Oliver

[57] ABSTRACT

An improved process for alkylating an alkylaromatic having at least one benzylic hydrogen atom with an olefinic compound comprising contacting the alkylaromatic under liquid phase conditions with an olefinic compound in the presence of at least one alkali metal activated by amine compound.

8 Claims, 2 Drawing Sheets

ALKYLATION OF ALKYLAROMATICS PROMOTED BY AMINE COMPOUND

This is a continuation of application Ser. No. 07/799,543 filed Nov. 27, 1991, now U.S. Pat. No. 5,198,594.

FIELD OF THE INVENTION

This invention relates to an improved process for the side-chain alkylation of an alkylaromatic compound with an olefinic compound. More particularly, this invention relates to an improved process for the side-chain alkylation of an alkylaromatic with an olefinic compound using a sonicated alkali metal promoter.

BACKGROUND OF THE INVENTION

The reaction of an alkylaromatic with an olefinic compound promoted by an alkali metal is a well-known process for adding the olefinic compound to the alkylaromatic compound. In these reactions, the alkylaromatic must have at least one benzylic hydrogen atom and, in the presence of a zero-valent alkali metal, a new covalent bond is formed between the carbon atom bearing the benzylic hydrogen atom and the olefinic compound. The overall process is exemplified by the following reaction showing the reaction of ethylene with toluene to form n-propylbenzene.

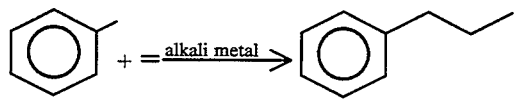

This type of reaction is commonly referred to as an alkylaromatic side-chain alkylation reaction. This reaction has also been described as a nucleophilic addition of the carbanion of the alkylaromatic to the olefinic compound. Other examples of this alkylation reaction include the reaction of toluene with styrene to form 1,3-diphenylpropane, and the reaction of propene with toluene to form isobutylbenzene (2-methyl-3-phenylpropane). As disclosed in U.S. Pat. Nos. 3,228,831 and 3,385,887, isobutylbenzene is a starting material for the preparation of Ibuprofen {α-methyl-4-(2-methylpropyl) benzeneacetic acid or 2-(4-isobutylphenyl) propionic acid}. Ibuprofen is a major, over-the-counter analgesic and anti-inflammatory pharmaceutical.

More recently, there has been an interest in preparing alkyl-substituted naphthalene compounds suitable for oxidation to naphthalenedicarboxylic acids. For example, 2,6-dimethylnaphthalene can be oxidized to 2,6-naphthalenedicarboxylic acid. 2,6-Naphthalenedicarboxylic acid is a monomer useful for preparing high performance polyester compositions. Although dimethylnaphthalenes such as 2,6-dimethylnaphthalene can be isolated from certain refinery streams, the concentration of the desired 2,6-dimethylnaphthalene in such streams is typically low and it is usually difficult to isolate the 2,6-dimethylnaphthalene in suitably large quantities. Consequently, synthetic procedures are useful for preparing dimethylnaphthalenes, and particularly 2,6-dimethylnaphthalene, starting from readily available materials. One such procedure, commonly referred to as the "Alkenylation Process", comprises reacting o-xylene with butadiene in the presence of a zero-valent alkali metal to form 5-ortho-tolylpentene (5-OTP). The alkali metal-promoted reaction of an alkylaromatic with a conjugated diene such as butadiene to form an olefinically substituted aromatic is referred to as an alkenylation reaction. The 5-OTP is subsequently cyclized to form 1,5-dimethyltetralin (1,5-DMT), the 1,5-DMT is dehydrogenated to 1,5-dimethylnaphthalene (1,5-DMN), and the 1,5-DMN is isomerized to the desired 2,6-dimethylnaphthalene (2,6-DMN). The "alkenylation step" of this overall process is depicted in the following equation:

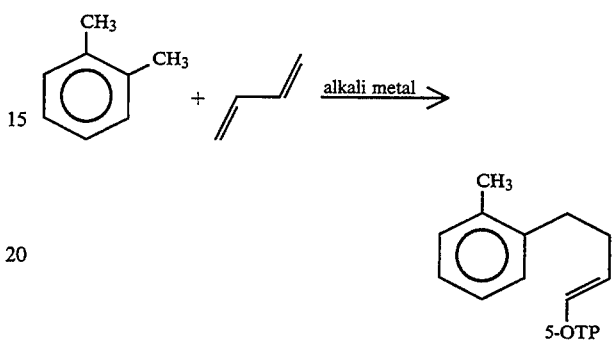

In order for the overall Alkenylation Process to be commercially successful for preparing 2,6-DMN—particularly because of the number of process steps involved—it is important to obtain a high yield in each step of the Alkenylation Process. Consequently, it is important for the preparation of 5-OTP from o-xylene and butadiene to proceed in high selectivity and high yield. Additionally, it is desirable to use as little alkali metal as possible because the alkali metal is expensive and usually not recyclable, and also because the reduced level of alkali metal is easier to quench. Residual alkali metal in the reaction product is quenched to avoid the possibility of ignition caused by alkali metal that subsequently comes in contact with moist air.

The art needs an improved process for the side-chain alkylation of alkylaromatic compounds with olefinic compounds. The present invention provides such an improved process wherein the alkali metal promoter is ultrasonically irradiated, i.e. sonicated, in order to produce a superior alkali metal promoter.

Methods for alkylating alkylaromatics with olefinic compounds using alkali metal promoters are taught in Pines and Stalick "Base-Catalyzed Reaction of Hydrocarbons and Related Compounds", pp. 240–308, Academic Press, New York, 1977. Processes for alkenylating xylenes with butadiene are disclosed in U.S. Pat. Nos. 3,766,288 and 3,953,535 to Shima et al. and in U.S. Pat. No. 3,244,758 to Eberhardt. A comprehensive discussion of the use of ultrasonic waves in synthetic organic chemistry, including the sonication of alkali metals, is disclosed in Einhorn et al., Synthesis, November 1989, pp. 787–813, c.f. pages 800–801, wherein it is disclosed that sonicated alkali metal can be used to prepare aromatic radical-anions, catalyze such reactions as the Dieckmann and Thorpe-Ziegler cyclizations, and to enolize ketones. These references do not, however, teach the use of sonication to improve the side-chain alkylation of an alkylaromatic with an olefinic compound.

SUMMARY OF THE INVENTION

A process for alkylating an alkylaromatic compound having at least one benzylic hydrogen atom with an olefinic compound comprises contacting the alkylaromatic compound under liquid phase conditions with the olefinic compound in the presence of at least one alkali metal activated by sonication.

DETAILED DESCRIPTION OF THE INVENTION

Figure 1:
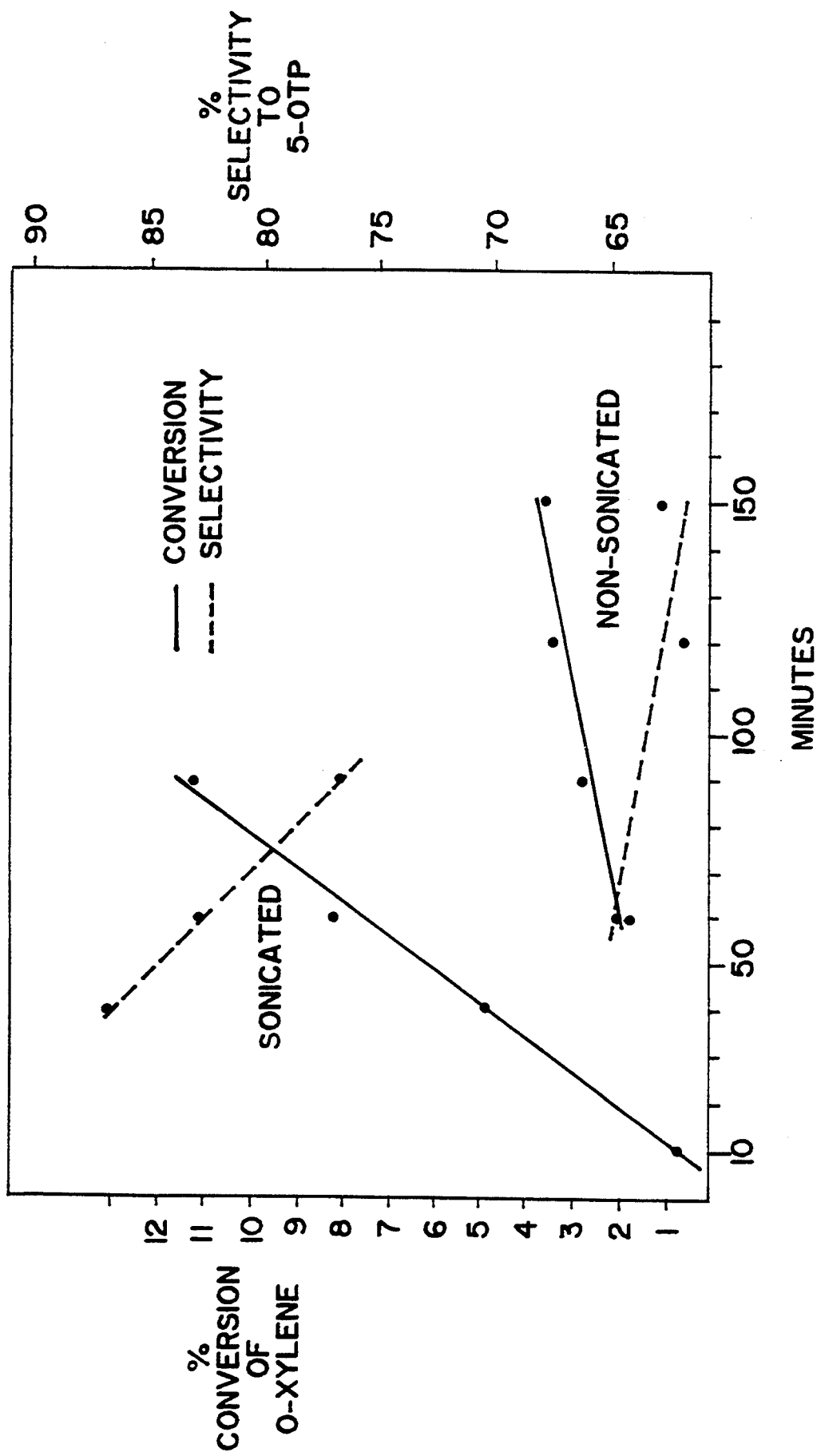
FIG. 1 shows o-xylene reaction rate data and 5-ortho-tolylpentene selectivity data for the semi-continuous mode reaction of o-xylene with butadiene promoted by sonicated alkali metal and non-sonicated (sheared) alkali metal.

In the process of this invention an alkali metal or mixture of alkali metals is irradiated with ultrasound and used to promote the condensation of an alkylaromatic compound with an olefinic compound in a liquid phase chemical reaction commonly known as a "side-chain alkylation reaction". The sonicated alkali metal provides for enhanced reaction rates. Additionally, enhanced selectivity to the desired alkylation product has also been observed.

The alkali metal promoter comprises any zero-valent alkali metal or mixture thereof that is at least partially and preferably totally liquid at the sonication temperature and, preferably, also at least partially liquid at the alkylation reaction temperature. In one embodiment of the present invention, the alkali metal is sonicated before it is added to the alkylation reaction mixture. In another embodiment, at least a pan of the alkylation reaction mixture is sonicated, i.e. the alkali metal is sonicated during the alkylation reaction. The alkali metals most useful for the process of this invention are lithium, sodium, potassium and cesium. Sodium and potassium are preferred, and potassium is the most preferred. It is advantageous to use certain mixtures of sodium and potassium because these mixtures exist as liquids over a wide temperature range. For example, sodium-potassium mixtures containing from about 45 to 90% potassium by weight are liquid above about 20° C. Particularly preferred is the eutectic mixture of sodium and potassium, commonly referred to as "NaK" or "nack". This mixture has a freezing point of −12.3° C. and, therefore, is completely liquid over a very wide temperature range, which makes handling easier and allows for a wide selection of reaction temperatures at which the alkali metal remains liquid. The true eutectic mixture is 77.2 wt. % potassium (67.3 atom percent) and 22.8 wt. % sodium (32.7 atom percent). Commercially available NaK, however, is about 22 wt. % sodium and about 78 wt. % potassium.

The alkylaromatic that can be alkylated in the process of this invention in any alkylaromatic that has at least one benzylic hydrogen atom. Most suitably the alkylaromatic is a hydrocarbon and contains 6 to about 20 nuclear carbon atoms and a total of 7 to 100 carbon atoms. The aromatic portion of the alkylaromatic compound can be a single aromatic ring such as benzene, or it can be a fused ring compound such as naphthalene, anthracene, pyrene, and the like. The aromatic portion can comprise aromatic rings joined by covalent bonds such as biphenyl compounds, or bridged by one or more heteroatom moieties such as an oxygen atom, or by hydrocarbon moieties such as:

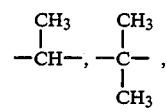

and the like.

The alkyl portion of the alkylaromatic must comprise at least one alkyl group that has at least one hydrogen on the benzylic carbon atom, i.e. on an alpha carbon atom. The alkyl group preferably contains 1 to about 4 carbon atoms and suitable alkyl groups include methyl, ethyl, isopropyl, n-propyl, secondary butyl, isobutyl, n-butyl, and the like. The alkyl group can also be substituted with, for example, an aromatic group such as a phenyl group, or with a keto group, ester group, ether group, tertiary amino group, N, N disubstituted amide group, and the like. Aromatic compounds having saturated ring groups such as the tetralins and indans are also suitable. While the alkylaromatic must contain at least one alkyl group that provides for at least one benzylic hydrogen atom, the actual number of alkyl groups that the alkylaromatic can contain is limited only by the number of positions on the aromatic portion of the molecule that can covalently bond with an alkyl moiety. Preferably, the aromatic compound contains from 1 to 4 alkyl groups. Specific examples of alkylaromatic compounds that can be alkylated with an olefinic compound according to the process of this invention include: toluene, o-, m- and p-xylene, 1,2,3- 1,2,4- and 1,3,5-trimethylbenzene, the tetramethylbenzenes, ethylbenzene, 1,2- 1,3- and 1,4-diethylbenzene, 1-methyl-4-ethylbenzene, isopropylbenzene, n-propylbenzene, n-butylbenzene, isobutylbenzene, 1- and 2-methylnaphthalene, dimethylnaphthalenes, diethylnaphthalenes, tetralin, indan, diphenylmethane, 1,2-diphenylethane, 1,1-diphenylethane, and the like.

Although not as preferred as purely hydrocarbon aromatic compounds, alkylaromatic compounds useful in the process of this invention include alkyl-substituted heterocyclic compounds such as, for example, alkyl-substituted pyridine, furan, thiophene, pyrrole and pyrazole compounds. Specific examples of alkyl-substituted heterocyclic compounds that can be used in the process of this invention include 2-, 3-, and 4-methylpyridine.

Preferred aromatic compounds that are alkylated according to the process of the invention are toluene, o-, m- and p-xylene, ethylbenzene, and isopropylbenzene. Most preferred are toluene and o-, m- and p-xylene.

The olefinic compound that is used to alkylate the alkylaromatic compound in the process of this invention is any compound containing at least one carbon-carbon double bond. Preferably, the olefin compound is a hydrocarbon containing about 2 to about 20 carbon atoms. More preferably, the olefin is selected from the group consisting of ethylene, propylene. butene-1, cis- and trans-2-butene, isobutene, and 1,3-butadiene. Most preferably, the olefinic compound is ethylene, propylene or 1,3-butadiene.

It is generally preferable to use a molar excess of the alkylaromatic compound relative to the olefinic compound. Employing an excess of the alkylaromatic compound reduces the formation of products resulting from the condensation of more than one olefinic compound per alkylaromatic compound. Suitably, the mole ratio of alkylaromatic compound to olefinic compound is at least about 1:1, preferably at least about 2:1, and, most preferably, at least about 5:1, respectively. Less than a stoichiometric amount of alkylaromatic compound to olefinic compound can be used, e.g. 0.5 to about 1.0 mole of alkylaromatic compound per mole of olefinic compound. However, under these conditions greater amounts of high molecular weight products are expected.

The temperature for the alkylation reaction is a temperature that provides for the desired alkylation reaction to proceed at a suitable rate. Preferably, the temperature should also be sufficient to maintain at least a portion of the alkali metal catalyst in the liquid state. Suitable temperatures are in the range of about 10° C. to about 300° C. The pressure for the reaction is a pressure sufficient to maintain at least a portion and preferably a major portion of the alkylaromatic in the liquid state, Suitable pressures range from about 0.01 atmosphere to about 100 atmospheres.

The alkylation reaction in the process of this invention can be conducted with or without a solvent. However, if the alkylaromatic compound is not a liquid at the reaction temperature, or if the ratio of alkylaromatic compound to olefinic compound is low, a suitable non-reactive solvent can be employed. For example, hydrocarbon solvents such as saturated aliphatic compounds including hexanes, cyclohexane, heptanes, octanes, white oil, decahydronaphthalene, and the like, as well as aromatic solvents free of benzylic hydrogen such as benzene, naphthalene, t-butylbenzene, etc. can be used, if desired.

The amount of alkali metal promoter used is an amount sufficient to permit the desired alkylation reaction to proceed at a reasonable rate. Typically, the amount of alkali metal is about 1.0 to about 10,000 parts by weight per million parts by weight of the alkylaromatic. More preferably, the amount of alkali metal is about 10 to about 500 parts, and most preferably about 10 to about 200 parts by weight per million parts by weight of alkylaromatic compound. One of the benefits of the process of this invention is the ability to use very low levels of the alkali metal promoter, i.e. about 1.0 to about 100 pans by weight per million pans by weight of alkylaromatic. The use of low levels of alkali metals provides for a lower cost process. Also, because the reaction mixture is typically quenched at the end of the reaction with a quenching agent such as water, an alcohol or other component such as carbon dioxide, to eliminate residual alkali metal or remove other reactive components, the use of reduced levels of alkali metal provides for less expensive, safer and more efficient quench procedures.

In the process of this invention, the alkali metal is sonicated prior to adding it to the alkylation reaction mixture and/or while it is in the reaction mixture by sonicating either a portion of or the entire reaction mixture. The exposure of the alkali metal to the ultrasound energy should be sufficient to provide for an activated catalyst. "Activated" means that the alkali metal that is sonicated provides for greater reaction rates than an equal amount of non-sonicated alkali metal. "Activated" also means that the same or improved results in terms of reaction yield and reaction selectivity can be achieved using a lower amount of sonicated alkali metal compared to non-sonicated alkali metal.

As stated hereinabove, the alkali metal is sonicated to an extent sufficient to provide for a more active alkali metal for the alkylation reaction. Generally, the alkali metal is sonicated while in a liquid medium. This liquid medium usually comprises the reaction solvent, the alkylaromatic compound, or the reaction mixture. Most preferably, the alkali metal is subjected to a source of ultrasound sufficiently powerful and for a period of time sufficient to provide for maximum dispersion of alkali metal in the liquid medium at a given set of conditions such as concentration of the alkali metal in the liquid medium, temperature of the mixture and the composition of the liquid medium. In a preferred means for practicing the process of this invention, the side-chain alkylation reaction is conducted in a continuous manner wherein one or a series of stirred tank reactors are used and the alkylaromatic, sonicated alkali metal promoter, and olefinic compound are continuously added to the reactor or reactors and a product mixture is continuously removed from the reactor, or last reactor in a series of reactors. A process for conducting an alkenylation reaction using a series of independently stirred reaction zones is disclosed in U.S. Pat. No. 3,865,889 to Mitchell, In the preferred continuous process of this invention, a mixture of the alkali metal and the alkylaromatic, with or without a solvent, is passed through a zone and irradiated with ultrasound before the alkali metal enters the reaction vessel. A suitable source of ultrasound is the 1,500 watt, 20 kilohertz (kHz) high volume ultrasonic liquid processing system available from Sonics & Materials, Inc., Danbury, Conn., although this invention is not limited by the type of generator used to create the ultrasonic energy.

Preferably, the ultrasound energy used to activate the alkali metal in the process of this invention has a frequency of at least about 18 kHz, preferably in the range of about 18 to 60 kHz, more preferably about 18 to about 25 kHz. In the preferred process of this invention the alkali metal promoter is exposed to ultrasound energy sufficient to produce a suspension of the alkali metal in the hereinabove described liquid medium wherein the suspended alkali metal promoter exists as small particles having an average particle size of no more than about 50 microns, preferably no more than about 10 microns, and most preferably no more than about 5 microns. These average particle sizes refer to the free particles and not to agglomerates of particles that can form. A suitable amount of ultrasonic power density is an amount of about 10 to about 10,000 watts per gram of alkali metal, preferably about 100 to about 1,000 watts per gram of alkali metal.

Activated alkali metal, particularly for the continuous process described hereinabove, can be prepared by subjecting the alkali metal in a liquid medium to ultrasound at an intensity equivalent to that obtained by passing about 10 to about 1,000, preferably about 100 to about 500 milliliters of a mixture of alkali metal and liquid medium, wherein the alkali metal is present in an amount from about 0.1 to about 100,000, preferably about 10 to about 1,000 parts by weight per million pans by weight of liquid medium, through the zone of the hereinabove described 1,500 watt, 20 kHz, Vibr Cell TM Ultrasonic Liquid Processing System equipped with a 1.0 inch diameter horn and a power setting from just above the minimum to the maximum, preferably in the range of about 10 to about 100. One ultrasonic generator or two or more ultrasonic generators arranged in series or in parallel can be employed depending on the amount of ultrasonic energy required to achieve the hereinabove described amount of ultrasound intensity.

The process of this invention is particularly suitable for reacting 1,3-butadiene with a xylene or with ethylbenzene in the presence of an alkali metal, the alkali metal preferably being potassium or a sodium/potassium mixture, to prepare tolylpentenes or phenylhexenes, respectively. The tolylpentenes and phenylhexenes can be cyclized to form dimethyltetralins which are dehydrogenated to dimethylnaphthalenes. For example, o-xylene can be alkenylated with 1,3-butadiene to form a mixture of 5-ortho-tolylpentene-1 and 5-ortho-tolylpentene-2, m-xylene can be alkenylated with 1,3-butadiene to form a mixture of 5-meta-tolylpentene-1 and 5-meta-tolylpentene-2; p-xylene can be alkenylated with 1,3-butadiene to form a mixture of 5-para-tolylpentene-1 and 5-para-tolylpentene-2; and ethylbenzene can be alkenylated with 1,3-butadiene to form a mixture of 5-phenylhexene-1 and 5-phenylhexene-2. The process of this invention is most preferably used for the alkenylation of o-xylene with 1,3-butadiene to form 5-ortho-tolylpentene-1 and 5-ortho-tolylpentene-2. Methods for cyclizing these tolylpentenes and phenylhexenes to dimethyltetralins are disclosed, for example, in U.S. Pat. No. 5,030,781 to Sikkenga, et al.

The alkenylation reaction of 1,3-butadiene with a xylene or with ethylbenzene is suitably conducted at a temperature in the range of about 10° C. to about 200° C., preferably about 80° C. to about 150° C. The pressure is suitably in the range of about 0.01 atmosphere to about 40 atmospheres, preferably about 1.0 atmosphere to about 3 atmospheres. The alkali metal is preferably potassium and more preferably a mixture of sodium and potassium containing from about 40 to about 90 wt. % potassium. An approximate NaK eutectic mixture, which can be obtained from Callery Chemical Company, Pittsburgh, Pa., is the most preferred source of alkali metal. The amount of alkali metal used is about 1.0 to about 1,000 parts by weight per million parts by weight of xylene or ethylbenzene, preferably about 10 to about 400 and most preferably about 10 to about 100 parts by weight per million parts by weight of xylene or ethylbenzene. The mole ratio of xylene or ethylbenzene to butadiene is suitably at least about 1:1, preferably at least about 2:1 and most preferably at least about 5:1. The alkenylation reaction of xylene or ethylbenzene with 1,3-butadiene can be conducted in the batch mode wherein all of the reactants are charged to a reaction zone initially and the reaction is allowed to proceed at a preselected reaction temperature and pressure. The reaction can also be conducted in the semi-continuous mode wherein at least one of the reactants is charged to the reaction zone during the course of the reaction. For example, essentially all of the alkali metal and essentially all of the xylene or ethylbenzene are charged to the reaction zone and the 1,3-butadiene is added to the reaction zone during the course of the reaction. Most preferably, the reaction of the 1,3-butadiene with the xylene or ethylbenzene is conducted in the continuous mode wherein the xylene or ethylbenzene, 1,3-butadiene, and alkali metal are each added to the reaction zone continuously and a product mixture containing the desired tolylpentene or phenylhexene is continuously removed from the reaction zone. The continuous process is most suitable for commercial scale operations. In each of the aforementioned batch, semi-continuous and continuous modes of operation, the alkali metal is sonicated before it is added to the reaction zone, while it is in the reaction zone, or both.

After the reaction mixture exits the reaction zone, it is typically quenched with water or an alcohol, or a mixture of water and an alcohol. The quenched product is subjected to a procedure for separating the product from the rest of the reaction mixture which is typically unreacted xylene or ethylbenzene. Unreacted xylene or ethylbenzene separated from the reaction mixture can be recycled. It is generally most preferable to operate the alkenylation reaction at low conversion of the xylene or ethylbenzene. In other words, operating so that the ratio of xylene or ethylbenzene to 1,3-butadiene is always high. Preferably, the conversion of xylene or ethylbenzene is no greater than about 30 percent, more preferably about 5 percent to about 15 percent.

In addition to sonicating the alkali metal promoter, we have also determined that the addition of an amine compound to the alkylation reaction improves the selectivity of the side-chain alkylation reaction with or without the use of sonication. For example, the addition of N,N,N,'N'-tetramethylethylenediamine to the reaction mixture for alkenylating o-xylene with 1,3-butadiene resulted in a substantial improvement in the selectivity for the conversion of o-xylene to 5-ortho-tolylpentene.

Suitable amine compounds include any amine that provides for improved selectivity for the hereinabove described alkylaromatic side-chain alkylation reaction. However, the preferable amines are tertiary amines such as a trialkylamine, a triarylamine or a tertiary amine comprising a combination of alkyl and aryl groups. The alkyl groups, which can be straight chain, branched or cyclic, suitably contain 1 to about 10 carbon atoms. The aryl groups, which can also be aralkyl, suitably contain 6 to about 30 carbon atoms. Such amines are represented by the structure:

wherein each R is independently alkyl, aryl or alkaryl, and wherein the alkyl group, which can be straight chain, branched or cyclic, contains about 1 to about 10 carbon atoms, and the aryl or alkaryl group contains about 6 to about 30 carbon atoms. Examples of suitable tertiary amines include: trimethyl-, triethyl-, tripropyl- and tributylamine; also N,N'-dimethyl- and N,N'-diethylcyclohexylamine, and the like.

Particularly, preferred amines are the amines containing at least two tertiary amine groups in the same molecule, and preferably wherein the two tertiary amine groups are separated by 1 to 4, and more preferably 2 carbon atoms. For example, those amines that have the following structure are suitable:

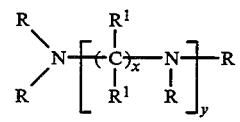

wherein R is independently a hydrocarbyl group having 1 to about 10 carbon atoms, and preferably methyl, $R^1$ is independently hydrogen or a hydrocarbyl group having 1 to about 10 carbon atoms, x is an integer from 1 to 4, inclusive, y is an integer $\geq 1$, preferably 1–10, inclusive, and when y > 1, x can vary from 1 to 4 within each molecule. Preferably, $R^1$ is hydrogen in the structure above. N,N'-disubstituted piperazine compounds, for example, trialkyl-1-(2-aminoethyl) piperazines are also suitable.

Specific amines suitable for use in the process of this invention that fall within one or more of the descriptions provided hereinabove include: N,N,N',N'-tetraalkylethylenediamine, N,N,N,'N'-tetraalkylpropylenediamine, N,N,N',N'-tetraalkyl-1,2-diaminocyclohexane, N,N,N',N'',N'''-pentaalkyldiethylenetriamine and N,N,N',N'',N''',N'''-hexamethyltriethylenetetraamine, wherein the alkyl groups are ethyl, propyl, n-butyl and, most preferably, methyl. Additional suitable amines include: 1-methylpyrrolidine, 1-methylpiperidine, 1,10-phenanthroline, N,N,N',N'-tetramethyldiaminomethane, N,N,N',N'-tetramethyl-1,4-diaminobutane, 1,4,7,10,13,16-hexamethyl-1,4,7,10,13,16,-hexaazacyclooctadecane, hexamethylenetetraamine, 1,4-dimethylpiperazine, N,N-dimethyl-1-aminonaphthalene, 1,4-diazabicyclo(2.2.2.)octane, 1,3,5-trimethylhexahydro-1,3,5-triazine, 1,4,8,11-tetramethyl-1,3,8,11-tetraazacyclotetradecane, and the like. N,N,N',N'-tetramethylethylenediamine and N,N,N',N'-tetramethyl-1,2-diaminocyclohexane are the most preferred amines.

The amine can be added to the reaction mixture along with the sonicated alkali metal or it can be added separately to the reaction mixture. The amine can also be present along with the alkali metal if the alkali metal is sonicated prior to adding it to the alkylation reaction mixture. The amount of amine used is an amount that provides for improved selectivity to the desired side-chain alkylation product. Suitably, at least about 0.1 mole of amine is used per mole of alkali metal. Preferably, at least about 0.5 mole and more preferably at least about 1 mole of amine is used per mole of alkali metal.

The following examples are presented to illustrate the invention without intending to limit the scope thereof.

EXAMPLES

The following Examples demonstrate the effectiveness of sonicating the alkali metal used for alkenylating an alkylaromatic. For Examples 1 and 2, a semi-continuous mode of operation was used wherein the o-xylene and alkali metal promoter were charged to the reactor and butadiene was added over a set time period. The conversion reported is the percentage of o-xylene consumed. Butadiene consumption was not measured. The percent selectivity reported for Examples1 and 2 was calculated by dividing the moles of o-tolylpentene formed by the moles of o-xylene converted and multiplying this quotient by 100.

In Examples 3-5, the alkenylation of o-xylene was conducted in a continuous manner. As described in more detail below, the o-xylene butadiene and NaK promoter were continuously added to the reaction vessel and a product mixture was continuously removed. In these Examples, all of the butadiene was consumed and the percent selectivity is based on the butadiene, i.e. the moles of 5-ortho-tolylpentene produced divided by the moles of butadiene added, the quotient being multiplied by 100. High o-xylene conversion is achieved by increasing the molar ratio of butadiene-to-o-xylene added to the reactor. The continuous-mode of operation is the most preferred mode of operating the process of this invention.

Example 1 (Comparative)

o-Xylene (96.0 g) previously dried over potassium metal for several days was added to a 500 ml round-bottom reaction flask equipped with an overhead mechanical stirrer, thermowell containing a thermocouple, gas dispersion tube, water condenser and sample port. The entire system was continuously purged with argon gas and NaK (0.0384 g) was injected into the reaction flask. The contents of the reaction flask were then heated to 126°-128° C. and, with stirring, purified butadiene gas was sparged into the reaction flask at a rate of about 71–74 ml/min. After approximately 30 minutes from the introduction of the butadiene, the reaction mixture turned to a dark red-brown color. The reaction was continued for approximately 2 hours before the reaction ceased. The percent conversion of o-xylene and the corresponding percent selectivity to 5-ortho-tolylpentene is reported in Table 1. This data is also plotted in FIG. 1.

Example 2

The same reaction apparatus as described in Example 1 was used for this Example. The reaction flask was placed in an ultrasonic cleaning bath (Bransonic Inc. Model Branson-2200) containing water at 7°-14° C. o-Xylene (97.7 g) previously dried as described in Example 1, was added to the reaction flask along with 0.0414 g of NaK. This mixture of o-xylene and NaK was sonicated for approximately 2.5 hours. During this time period, the mixture turned from a clear liquid containing distinct particles of NaK to an opaque, blue-grey-colored liquid. The reaction flask was removed from the ultrasonic bath and the temperature of the mixture was raised to 125° C. before butadiene was introduced into the reactor. Within 10 minutes the reaction mixture turned to the characteristic dark, red-brown color. At this time, 0.7% conversion of the o-xylene already occurred. The addition of the butadiene was continued until 11% of the o-xylene was converted. The percent conversion of this o-xylene and the corresponding percent selectivity to 5-ortho-tolylpentene is reported in Table 1. This data is also presented in FIG. 1.

A comparison of the data from Example1 with the data from Example 2 clearly demonstrates that sonicating the NaK promoter results in a superior reaction rate. This data also demonstrates that the sonicated alkali metal provided for superior selectivity to the desired 5-ortho-tolylpentene.

Example 3

For this example, the reaction of butadiene with o-xylene was conducted in an apparatus having two, series-arranged continuous stirred tank reactors, each constructed of carbon steel. The capacity of each reactor was about 3.5 gallons and they were maintained at about half-fill level during the course of the reaction. Each reactor was agitated at a stirring rate of 330 rpm, and each was equipped with cooling coils to maintain predetermined reaction temperatures. The contents from the first reactor overflowed into the second reactor through an overflow pipe. Dry o-xylene was pumped into the first reactor at a flow rate of about 170 g/min. Dry butadiene was added equally to each reactor at a total flow rate of about 10–30 grams/min. A NaK mixture was prepared batchwise by mixing dry o-xylene (approx. 1 gallon) with NaK promoter (20 g) for about 1 hour at 500 rpm at room temperature in a separate vessel. This treatment constitutes mechanical shearing. This mixture was transferred to a promoter feed vessel, which was equipped with a stirrer operating at 150 rpm. The mixture of NaK and o-xylene in the feed vessel was metered into the first reaction vessel at a rate of 3 to 15 grams/min. The reactor vessels were operated at 115° C. and at atmospheric pressure. The residence time in each reactor was about 1 hour.

Figure 2:
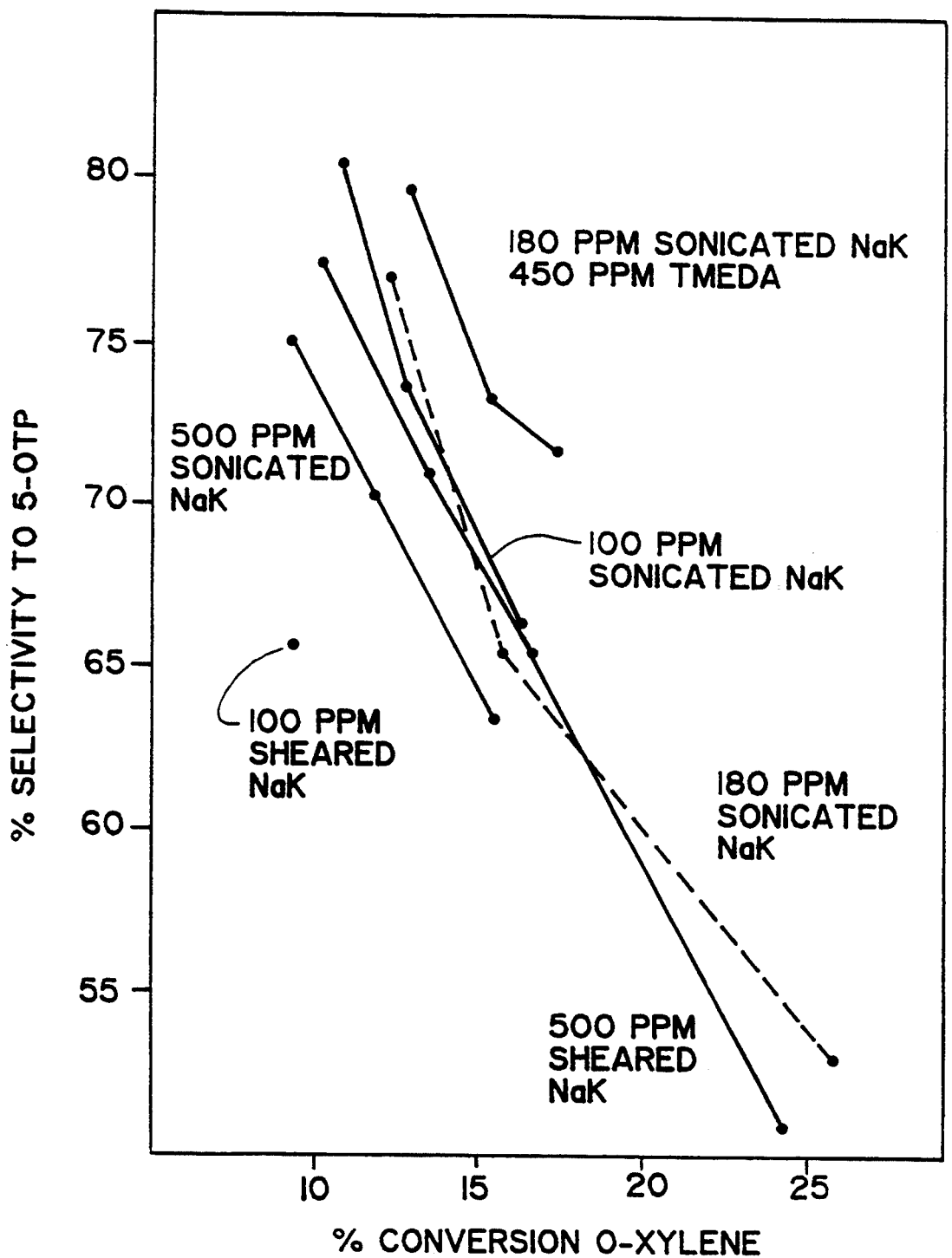
FIG. 2 shows selectivity data for the continuous-mode reaction of o-xylene with butadiene to form 5-ortho-tolylpentene promoted by sonicated alkali metal, non-sonicated (sheared) alkali metal, and sonicated alkali metal in combination with N,N,N',N'-tetramethylethylenediamine (TMEDA).

Table II lists the data for the selectivity to the desired 5-ortho-tolylpentene based on butadiene. The conversion of the o-xylene is also provided. These data were taken under conditions where the NaK was mechanically sheared, i.e. no ultrasound was used. These data are also presented in FIG. 2. The ppm NaK refers to the parts of NaK by weight per million parts of o-xylene.

Example 4

The reaction of o-xylene and butadiene was conducted in the same apparatus as that described in Example 3 except that after exiting the promoter feed vessel, the o-xylene mixture of o-xylene and NaK from the feed vessel was passed through the cell of a Vibr Cell T-M High Volume Ultrasonic Liquid Processing System, manufactured by Sonics & Materials, Inc., equipped with a 1.0 inch diameter titanium horn, A power setting of about 10-20 on the power supply was used. The data obtained for the 5-ortho-tolylpentene produced with the sonicated NaK is reported in Table II and also provided in FIG. 2.

A comparison of the data from the reaction conducted using the sonicated NaK to the reaction conducted using mechanically sheared NaK demonstrates that 100 ppm sonicated NaK performs substantially better than 100 ppm mechanically sheared NaK. Furthermore, at the lower conversions of o-xylene, 100 ppm of sonicated NaK provided for superior selectivity to 5-ortho-tolylpentene compared to 500 ppm of mechanically sheared NaK. This data also demonstrates that 500 parts per million of sonicated NaK provides for lower selectivity at a given conversion than 500 ppm of sheared NaK. It is believed that the sonicated NaK promoter is highly active and, at high concentrations, the sonicated NaK may actually reduce selectivity to 5-ortho-tolylpentene. In commercial-scale operations, the reaction is typically run at low conversion in order to obtain maximum selectivity.

Example 5

The procedure of Example 4 was repeated using 180 ppm by weight NaK and 450 ppm by weight N,N,N',N'-tetramethylethylenediamine (TMEDA). These data are presented in Table III, and the data are also in graphic from in FIG. 2. These data show that the use of TMEDA in conjunction with the NaK alkali metal promoter results in further enhancement of the selectivity for the production of 5-ortho-tolylpentene.

TABLE I

| Reaction Time[a] | Example 1 (No Sonication) | | Example 2 (Sonication) | |
|---|---|---|---|---|
| | % Conv.[b] | % Sel.[c] | % Conv.[b] | % Sel.[c] |
| 10 | | | 0.7 | 100 |
| 40 | | | 4.8 | 87 |
| 60 | 1.7 | 65 | 8.1 | 83 |
| 90 | 2.7 | 64 | 11.1 | 77 |
| 120 | 3.4 | 62 | | |

TABLE I-continued

| Reaction Time[a] | Example 1 (No Sonication) | | Example 2 (Sonication) | |
|---|---|---|---|---|
| | % Conv.[b] | % Sel.[c] | % Conv.[b] | % Sel.[c] |
| 150 | 3.4 | 63 | | |

[a]Time in minutes from addition of butadiene.
[b]Percent conversion of the o-xylene.
[c]Percent of the o-xylene converted that produced 5-ortho-tolylpentene.

TABLE II

| NaK Concentration[a] (PPM) | No sonication[b] | | Sonication | |
|---|---|---|---|---|
| | % o-Xylene Conversion | % 5-OTP Selectivity | % o-Xylene Conversion | % 5-OTP Selectivity |
| 100 | 9.27 | 65.59 | 10.67 | 80.38 |
| | | | 12.57 | 73.61 |
| | | | 16.16 | 66.27 |
| 180 | | | 12.01 | 77.00 |
| | | | 15.83 | 65.34 |
| | | | 25.78 | 53.01 |
| 500 | 10.10 | 77.40 | 9.20 | 75.14 |
| | 13.40 | 71.00 | 11.70 | 70.09 |
| | 16.70 | 65.30 | 15.37 | 63.38 |
| | 24.19 | 50.96 | | |

[a]Parts per million by weight of NaK in o-xylene.
[b]Mechanically sheared.

TABLE III

| % o-Xylene Conversion[a] | % 5-OTP Selectivity |
|---|---|
| 12.84 | 79.70 |
| 15.26 | 73.46 |
| 17.34 | 71.97 |

Certain embodiments of the present invention have been set forth in the preceding description of the invention. However, alternative embodiments and various modifications will be apparent to those skilled in the art. These alternatives and modifications are considered to be equivalents and within the spirit and scope of the present invention.

Having described the invention, that which is claimed is:

1. A process for alkylating an alkylaromatic compound having at least one benzylic hydrogen atom with an olefinic compound comprising contacting the alkylaromatic under liquid phase conditions with an olefinic compound in the presence of at least one zero valent alkali metal and in the presence of an amine compound.

2. The process of claim 1 wherein the amine compound is a tertiary amine.

3. The process of claim 1 wherein the amine compound contains at least two tertiary amine groups in the same molecule.

4. The process of claim 1 wherein the amine compound has structure:

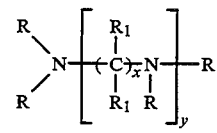

wherein R is independently a hydrocarbyl group having 1 to about 10 carbon atoms, $R_1$ is independently hydrogen or a hydrocarbyl group having 1 to about 10 carbon atoms, x is an integer from 1 to 4, inclusive, y is an integer from 1–10, inclusive, and when y > 1, x can vary from 1 to 4 within each molecule.

5. The process of claim 1 wherein the amine is selected from the group consisting of 1-methylpyrrolidine, 1-methylpiperidine, 1,10-phenanthroline, N,N,N',N'-tetramethyldiaminomethane, N,N,N',N'-tetramethyl-1,4-diaminobutane, 1,4,7,10,13,16-hexamethyl-1,4,7,10,13,16-hexaazacyclooctadecane, hexamethylenetetraamine, 1,4-dimethylpiperazine, N,N-dimethyl-1-aminonaphthalene, 1,4-diazabicyclo(2.2.2.)octane, 1,3,5-trimethylhexahydro-1,3,5-triazine, and 1,4,8,11-tetramethyl-1,3,8,11-tetraazacyclotetradecane.

6. The process of claim 1 wherein the amine is selected from the group consisting of N,N,N'N'-tetramethylethylenediamine and N,N,N',N'-tetramethyl-1,2-diaminocyclohexane.

7. The process of claim 1 wherein the alkylaromatic is o-xylene and olefinic compound is 1,3-butadiene.

8. The process of claim 6 wherein the alkylaromatic is o-xylene and the olefinic compound is 1,3-butadiene.

* * * * *

UNITED STATES PATENT AND TRADEMARK OFFICE
CERTIFICATE OF CORRECTION

PATENT NO. : 5,334,796     Page 1 of 2
DATED     : August 2, 1994
INVENTOR(S) : Lawrence D. Lillwitz, et al.

It is certified that error appears in the above-indentified patent and that said Letters Patent is hereby corrected as shown below:

| Col. | Line |
| --- | --- |
| 4 | 5 |

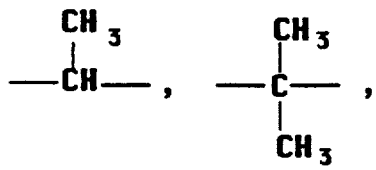

should read:

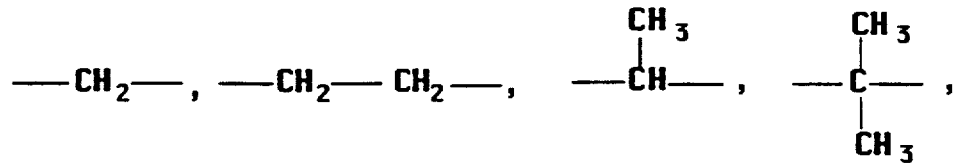

UNITED STATES PATENT AND TRADEMARK OFFICE
CERTIFICATE OF CORRECTION

PATENT NO. : 5,334,796

DATED : August 2, 1994

INVENTOR(S) : Lawrence D. Lillwitz, et al,

It is certified that error appears in the above-indentified patent and that said Letters Patent is hereby corrected as shown below:

| Col. | Line | |
|---|---|---|
| 5 | 47 | "about 100 pans by weight per million pans by weight" should read --about 100 parts by weight per million parts by weight-- |
| 6 | 62 | "1,000 parts by weight per million pans" should read --1,000 parts by weight per million parts-- |
| 12 | 32 | underneath Table III, the following footnote should be inserted --ᵃ Reaction mixture contained 180 parts by weight of NaK and 450 parts by weight of TMEDA per million parts of o-xylene.-- |

Signed and Sealed this

Twenty-seventh Day of February, 1996

Attest:

BRUCE LEHMAN

Attesting Officer

Commissioner of Patents and Trademarks